(12) United States Patent
Ryan et al.

(10) Patent No.: US 6,923,807 B2
(45) Date of Patent: Aug. 2, 2005

(54) HELICAL DEVICE AND METHOD FOR AIDING THE ABLATION AND ASSESSMENT OF TISSUE

(75) Inventors: Thomas P. Ryan, Flemington, NJ (US); David G. Reed, Langhorne, PA (US)

(73) Assignee: Ethicon, Inc., Somerville, NJ (US)

( * ) Notice: Subject to any disclaimer, the term of this patent is extended or adjusted under 35 U.S.C. 154(b) by 182 days.

(21) Appl. No.: 10/184,042

(22) Filed: Jun. 27, 2002

(65) Prior Publication Data

US 2004/0002699 A1 Jan. 1, 2004

(51) Int. Cl.[7] .............................................. A61B 18/18
(52) U.S. Cl. ........................ 606/41; 607/101; 607/127
(58) Field of Search .............................. 606/41, 45–50; 607/101–102, 127

(56) References Cited

U.S. PATENT DOCUMENTS

| | | | |
|---|---|---|---|
| 5,405,376 A | * | 4/1995 | Mulier et al. ................ 607/127 |
| 5,507,743 A | * | 4/1996 | Edwards et al. .............. 606/41 |
| 5,536,267 A | * | 7/1996 | Edwards et al. .............. 606/41 |
| 5,935,138 A | | 8/1999 | McJames, II et al. |
| 5,980,516 A | * | 11/1999 | Mulier et al. ................ 606/41 |
| 6,102,887 A | * | 8/2000 | Altman ........................ 604/22 |
| 6,112,123 A | * | 8/2000 | Kelleher et al. .............. 607/98 |
| 6,280,441 B1 | * | 8/2001 | Ryan ........................... 606/45 |
| 6,497,704 B2 | * | 12/2002 | Ein-Gal ....................... 606/41 |
| 6,716,196 B2 | * | 4/2004 | Lesh et al. ............. 604/164.01 |

* cited by examiner

*Primary Examiner*—Michael Peffley
(74) *Attorney, Agent, or Firm*—McCarter & English, LLP; Ralph W. Selitto, Jr.

(57) ABSTRACT

A helical needle is attached to a surgical probe to aid in the insertion of the probe into a tissue mass. The tip of the helical needle penetrates the tissue mass in advance of the tip of the probe. The probe is rotated to push the helical shaft of the needle into the tissue mass in the direction of rotation. As the helical shaft advances into the tissue mass, the probe advances with it. Rotating the probe in the opposite direction causes the helical needle and probe to withdraw from the tissue mass. Rotation of the probe and needle is more effective in penetrating rubbery and calcified growths than the conventional method of pushing the probe, and it enables the precise placement of the probe. The helical needle also enables insertion of the probe in situations where an inconvenient angle of entry makes it difficult to push the probe along.

1 Claim, 7 Drawing Sheets

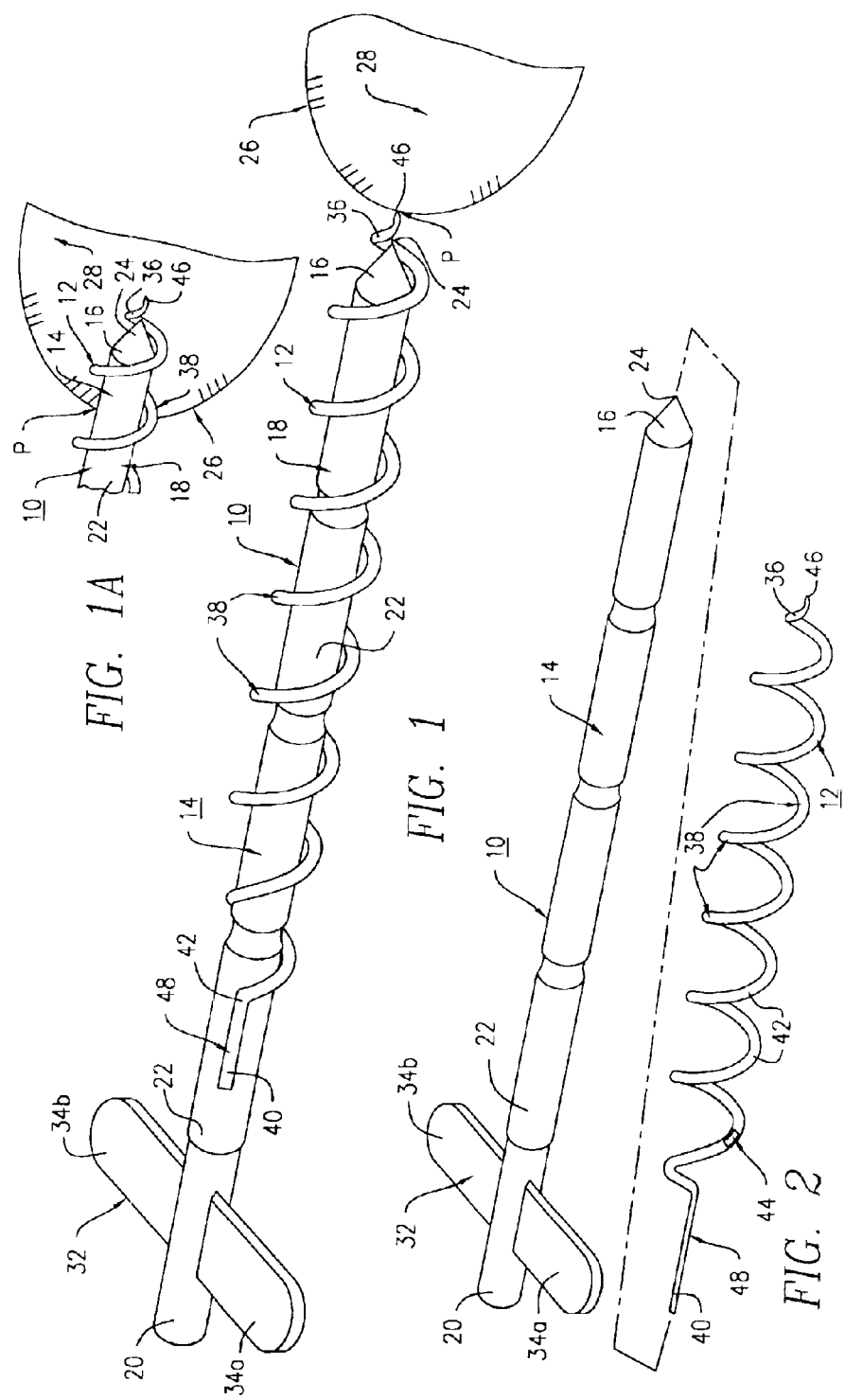

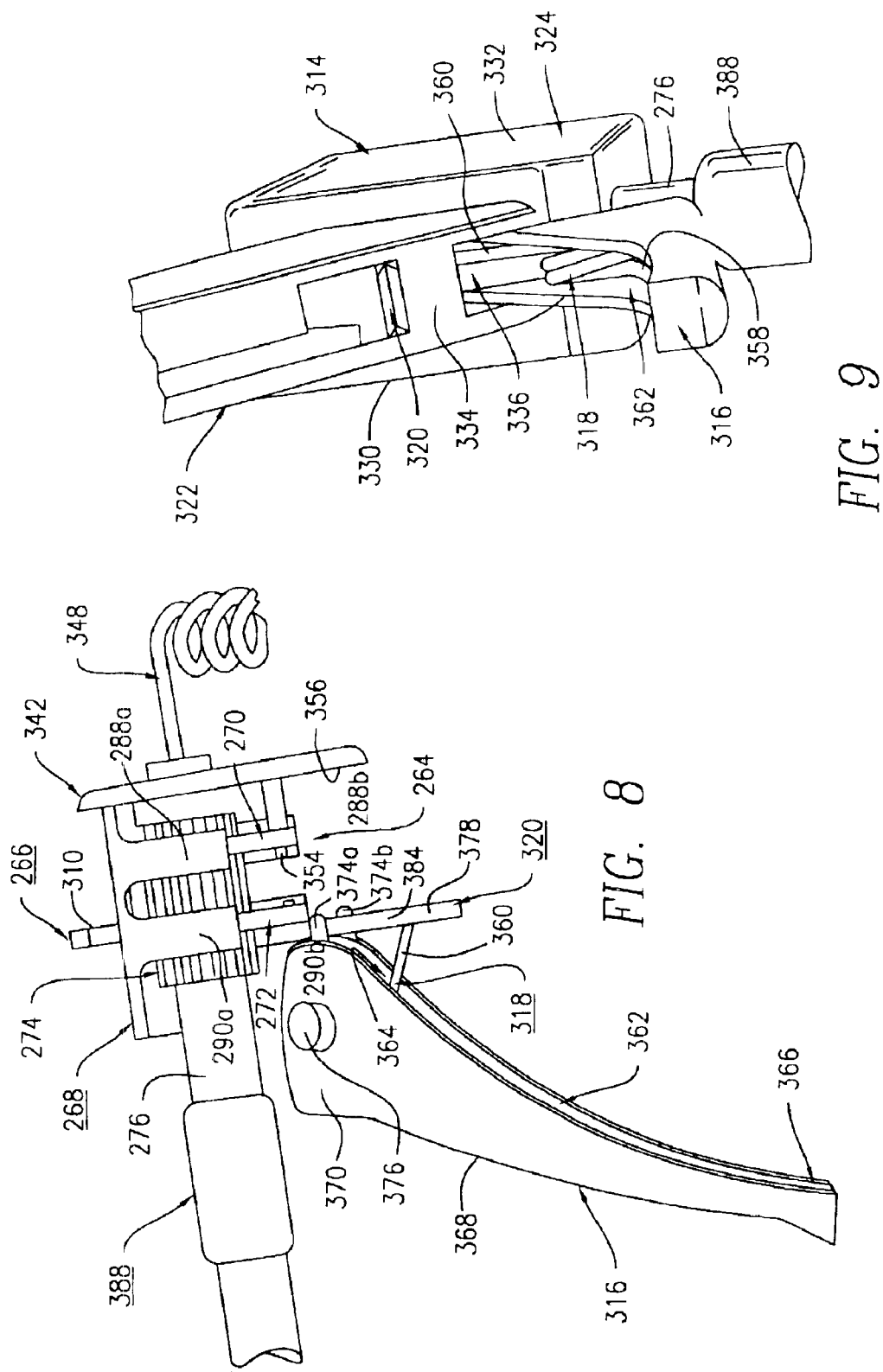

HELICAL DEVICE AND METHOD FOR AIDING THE ABLATION AND ASSESSMENT OF TISSUE

FIELD OF THE INVENTION

The present invention relates generally to a surgical device to assess the performance of thermal treatment of diseased tissue. More particularly, a surgical device utilizes a helical needle to facilitate entry of a surgical treatment probe into the diseased tissue with minimal difficulty. The diseased tissue may be malignant or benign.

BACKGROUND OF THE INVENTION

The laparoscopic surgical technique of thermal ablation has known applications as a minimally-invasive procedure for reducing the volume of diseased tissue masses. In a typical thermal ablation procedure, a probe carrying a thermal energy source is inserted into the targeted tissue mass to a depth where the treatment will be most effective. The tissue is then heated to a temperature at which it coagulates, killing the treated tissue. The probe is removed and the dead tissue is left in place to be resorbed by the affected organ or tissue area. In some treatments, the probe is cooled to a cryogenic temperature to freeze the tissue rather than heat it.

The insertion and proper placement of the probe may become problematic in the treatment of some tissue masses that comprise rubbery and/or calcified tissue, such as fibroid growths of uterine muscular tissue (i.e., myomas). Such tissue masses tend to resist penetration and deflect the movement of the probe. The difficulty of inserting the probe into the tissue mass increases in cases where the laparoscopic opening affords an inconvenient angle of entry for the probe.

Laparoscopic probes in the prior art, including thermal probes, have been made in the form of thin needles, typically about one (1) mm in diameter, such that the probe may be inserted with relatively little resistance from the tissue mass. Unfortunately, these small diameter probes bend easily when inserted into the resisting tissue, resulting in misalignment within the tissue mass and reducing the effectiveness of the thermal ablation treatment. Moreover, straight, needle-like probes that are easily inserted are susceptible to being accidentally displaced during the treatment procedure. Thicker, more rigid probes would be less likely to bend, but, because of their thickness, would be more difficult to insert into a tissue mass than the thinner flexible probes.

There remains a need for a surgical assistance device that aids the surgeon in inserting a laparoscopic probe into a resisting tissue mass. Such a device should allow precise placement of the probe within the tissue mass and resist accidental displacement. It is desirable that the device aid the insertion of relatively thick and rigid probes, in the range of 2–5 mm diameter. The device should be usable for laparoscopic surgery, open surgery, percutaneously or through natural body openings such as the vagina.

SUMMARY OF THE INVENTION

In one aspect, the present invention comprises a helical needle affixed to a laparoscopic probe so that the distal end of the needle extends beyond the distal end of the probe. A preferred embodiment of the invention comprises a helical needle having a helical shaft section that encompasses the straight shaft of the probe. More preferably, the helical needle is terminated by a sharp tip, for puncturing tissue, located on a common axis with the helical shaft section of the helical needle and the straight shaft section of the probe.

Another aspect of the invention provides a means for assessing the performance of thermal ablation of a tissue mass. In a preferred embodiment of this aspect of the invention, a number of thermal sensors are provided on the helical shaft section of a helical needle affixed to a thermal treatment probe to measure the temperature of the heated tissue.

In another aspect of the invention, the probe is provided with a driving means to selectively rotate the probe in a direction that drives the helical needle into a tissue mass or in an opposite direction to wind the helical needle out of the tissue mass. One preferred embodiment of this aspect of the invention provides a handle with opposed turning tabs at the proximal end of the probe. In another preferred embodiment, the rotation of the probe is driven by a motorized device having a directional control switch. A third preferred embodiment employs a manually operated ratchet assembly with an independently movable ratchet and pawl to control the direction of rotation of the ratchet gear that drives the probe.

A fourth aspect of the invention includes methods for inserting a laparoscopic probe into a tissue mass. The probe is provided with a helical needle affixed thereto such that the distal end of the needle extends past the distal end of the probe. In a preferred method, the tissue mass is punctured with the distal end of the needle and the probe is rotated such that the helical needle advances into the tissue mass in the direction of rotation, thereby advancing the probe into the tissue mass. In another preferred embodiment, the probe is rotated by a driving means that is calibrated to allow precise rotation of the probe.

The use of a helical needle in combination with a laparoscopic probe enables the probe to penetrate a tissue mass by rotation when the condition of the tissue or an inconvenient angle of entry would make it difficult to insert the probe by the conventional method of pushing it in an axial direction. The assistance provided by the helical needle also enables the use of probes having larger diameters than the one (1) mm probes that are presently preferred. The combination of probe and helical needle disclosed herein may be used advantageously in laparoscopic surgery, open surgery, hysteroscopic surgery or for entry through natural body orifices.

BRIEF DESCRIPTION OF THE DRAWINGS

For a more complete understanding of the present invention, reference is made to the following detailed description of the present invention considered in conjunction with the accompanying drawings, in which:

FIG. 1 is a perspective view of a surgical probe comprising a laparoscopic probe and a helical needle attached thereto constructed in accordance with a first exemplary embodiment of the present invention;

FIG. 1A is a perspective view of the surgical probe of FIG. 1 illustrating an advanced entry of the probe and helical needle within the tissue mass;

FIG. 2 is an exploded perspective view of the surgical probe of FIG. 1 showing the laparoscopic probe and helical needle;

FIG. 8 is a perspective view of the ratchet-type screw assembly of FIG. 7 showing the pull level attached to the ratchet mechanism;

FIG. 9 is a rear perspective view of the ratchet-type screw assembly of FIG. 5 showing the pull lever attached to a handle housing;

DETAILED DESCRIPTION OF THE EXEMPLARY EMBODIMENTS

Figures 3A, 3B, 4:
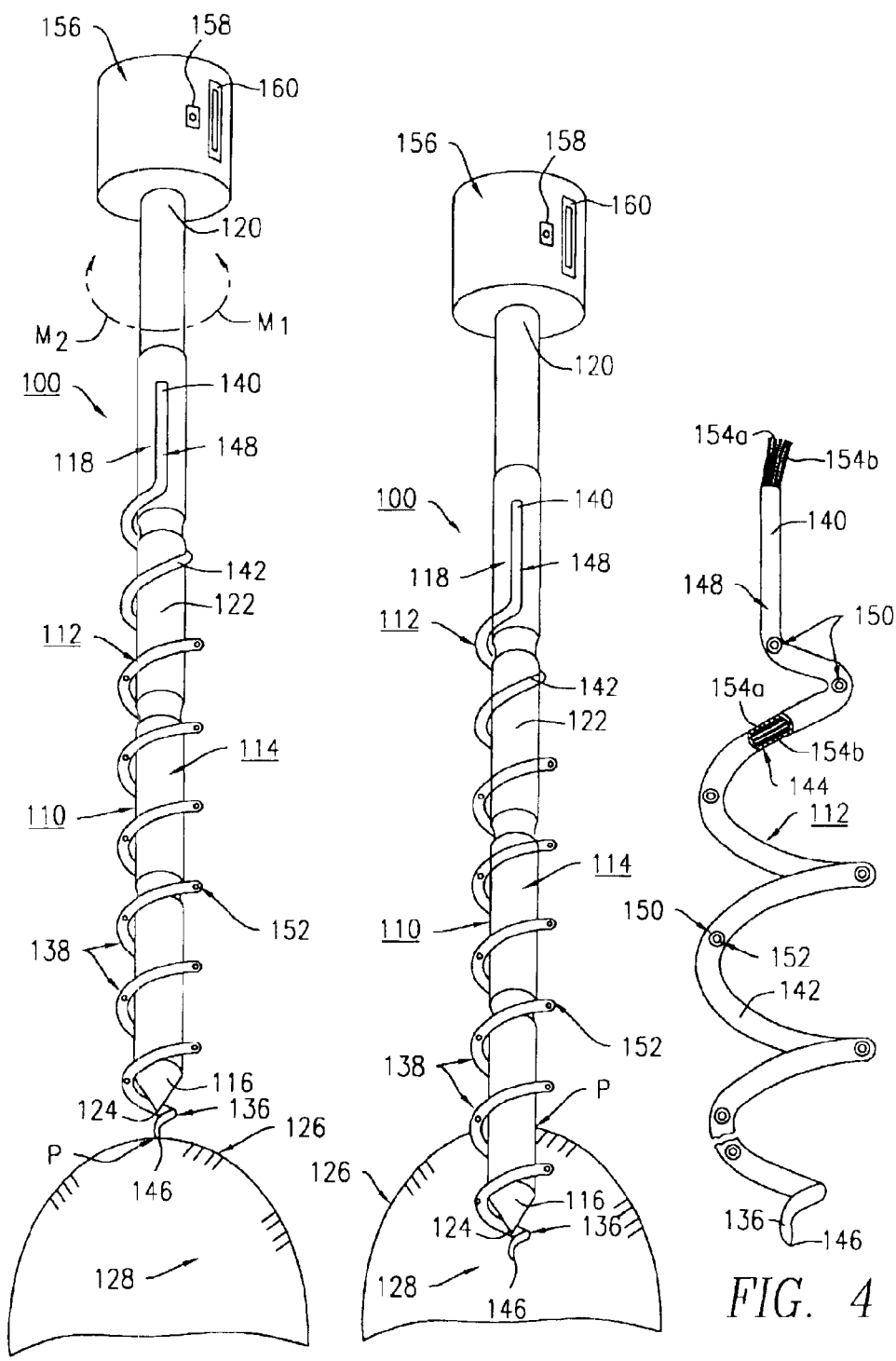
FIG. 3A is a perspective view of a surgical probe comprising a laparoscopic probe and a helical needle attached thereto constructed in accordance with a second exemplary embodiment of the present invention illustrating the initial entry of the helical needle into a tissue mass using a motorized device.
FIG. 3B is a perspective view of the surgical probe of FIG. 3A illustrating an advanced entry of the probe within the tissue mass using a motorized device.
FIG. 4 is a perspective view of the helical needle of FIG. 3A showing a plurality of thermal sensors within the helical needle.

Referring to FIGS. 1, 1A and 2, there is shown a probe 10 of a type used in laparoscopic surgical procedures in combination with a helical needle 12. The probe 10, as shown in FIG. 2, includes a straight needle-like element 14 having a distal end 16, an elongated shaft section 18, a proximal end 20, and an exterior wall surface 22. The distal end 16 of needle-like element 14 is terminated by a sharp tip 24 for entering a tissue mass 28 such as a myoma, tumor or other unwanted growth (see FIG. 1A). The proximal end 20 of needle-like element 14 includes a handle member 32 having a pair of opposing turning tabs 34a, 34b attached to the exterior wall surface 22 for use in driving the helical needle 12 and probe 10 into the tissue mass 28. The needle-like element 14 is made from a rigid material, such as stainless steel, ceramic or a rigid plastic such as teflon. The needle-like element 14 preferably has a length in a range from about 20 mm to about 100 mm and a diameter in a range of from about 2.0 mm to about 5.0 mm. The probe 10 may have an energy source (not shown) connected thereto for providing the thermal energy to ablate the targeted tissue mass 28. The energy source may be in the form of RF electrodes, ultrasound transducers, microwave transducers, cryogenic, or other energy sources adapted to provide localized treatment of the tissue mass 28.

Referring to FIG. 2, the helical needle 12 has a distal end 36, a helically-shaped shaft section 38, a proximal end 40, an exterior wall surface 42 and an interior channel 44. The distal end 36 of the helical needle 12 is terminated by a sharp tip 46 for puncturing the tissue wall 26 and assisting the entry of helical needle 12 into the tissue mass 28 (see FIG. 1A). The proximal end 40 of the helical needle 12 has an attachment section 48 for affixing the helical needle 12 to the needle-like element 14. The helical needle 12 is preferably made from a rigid material, such as stainless steel, ceramic or a rigid plastic such as teflon, or of a resilient "shape memory" metallic alloy, such as nitinol. The helical needle preferably has a length in a range from about 25 mm to about 105 mm, and a thickness in a range of from about 0.50 mm to about 1.5 mm. The diameter of the helically-shaped shaft 38 should be sufficiently large to allow the helically-shaped shaft 38 to encompass the needle-like element 14.

The helically-shaped shaft 28 of the helical needle 12 is disposed so as to encompass the needle-like element 14 of the probe 10 (see FIG. 1) with the sharp tip 46 of the helical needle 12 extending distally beyond the sharp tip 24 of the needle-like element 14. The attachment section 48 of the helical needle 12 is affixed to the elongated shaft section 18 such that the helical needle 12 and needle-like element 14 cannot be moved in a rotational or axial direction independently of each other. The attachment section 48 may be affixed to the exterior wall surface 22 of the needle-like element 14 by means such as soldering, welding, epoxy gluing, or laser welding, by insertion in a receiving groove (not shown) on the elongated shaft 18, or by the use of mechanical devices (e.g., connecting straps). Other means for affixing the helical needle 12 to the needle-like element 14 will be obvious to those persons skilled in the mechanical arts.

The helical needle 12 assists the entry of the probe 10 into the tissue mass 28, as the following example illustrates. Referring again to FIGS. 1 and 1A, the probe 10 is positioned with its distal end 16 pointing toward the tissue mass 28 with the sharp tip 46 of the helical needle 12 in contact with the tissue wall 26. The probe 10 is moved toward the tissue mass 28 such that sharp tip 46 penetrates the tissue wall 26 at entry point P. The probe 10 is then rotated so as to wind the helically-shaped shaft 38 of the helical needle 12 into the tissue mass 28. The helical shape of the shaft 38 causes the helical needle 12 to advance into the tissue mass 28 in a screw-like manner, i.e., the helical needle 12 advances in an axial direction by a predetermined distance for each rotation of the shaft 38. Because the helical needle 12 is rigidly affixed to the probe 10, the probe 10 also advances into the tissue mass 28 as the helically-shaped shaft 38 is wound into the tissue mass 28. The probe 10 may be removed from the tissue mass 28 by rotating the probe 10 so as to wind the helically-shaped shaft 38 out of the tissue mass. The advancement or removal of the probe 10 may be assisted by applying an axially-directed force to the probe 10 as it is rotated.

A second exemplary embodiment 100 of the present invention is shown in FIGS. 3A, 3B and 4. Elements shown in FIGS. 3A, 3B and 4 which correspond to the elements described above with reference to FIGS. 1, 1A and 2 have been designated by corresponding reference numbers increased by one hundred. The second exemplary embodiment 100 is constructed and operates in the same manner as the first exemplary embodiment 10, unless it is otherwise stated.

Referring to FIGS. 3A, 3B and 4, the helical needle 112 includes a plurality of openings 150, each opening 150 being adapted to receive a thermal sensor 152 therein. Each of the thermal sensors 152 has a pair of conductive leads 154a, 154b attached thereto for electrically activating the corresponding thermal sensor 152. Preferably, the thermal sensors 152 are spaced apart from each other by distances between about 2 mm and about 20 mm. As can be seen in FIG. 4, each of the thermal sensors 152 is exposed at the exterior wall surface 142 of the helically-shaped shaft 138 of helical needle 112 through the corresponding opening 150. The conductive leads 154a, 154b are routed within the interior channel 144 from the corresponding thermal sensor 150 and the proximal end 140 of the helical needle 112. Each of the thermal sensors 152 and the corresponding conductive leads 154a, 154b may be attached to openings 150 and to the interior channel 144 by epoxy cement, soldering, laser welding, or other means of attachment known in the arts. The helical needle 112 may be fabricated by inserting the thermal sensors 152 and their corresponding conductive leads 154a, 154b into the interior channel 144 of a straight pre-formed needle (not shown) having openings 150, then bending the straight needle into the helical configuration of needle 112. The helical needle 12 may also be encased in a shrink wrap layer (not shown) that is thin, durable and biocompatible to protect the thermal sensors and prevent them from interfering with the insertion of the helical needle 112 into the tissue mass 126.

Referring again to FIGS. 3A and 3B, it can be seen that the proximal end 120 of the probe 110 does not include a handle member 32 such as that included in the first embodiment 10 (see FIG. 1). The proximal end 120 of the probe 110 includes a motorized device 156, which may include an AC, DC or stepper motor, for rotating the probe 110 in a rotational direction $M_1$ or an opposite rotational direction $M_2$, as required to insert or withdraw the probe 110 and helical needle 112 from the tissue mass 128. The motor 156 includes an on/off switch 158 to start or stop the motor of motorized device 156 and a directional switch 160 to switch the direction of rotation provided by the motorized device 156 between rotational direction $M_1$ and rotational direction $M_2$.

The motorized device 156 assists the entry of the probe 110 into the tissue mass 128, as the following example shows. Referring again to FIGS. 3A and 3B, the probe 110 is positioned with its distal end 116 pointing toward the tissue mass 128 with the sharp tip 146 of the helical needle 112 in contact with the tissue wall 126 at entry point P. The motorized device 156 is started by means of on/off switch 158 and the directional switch 160 is set such that the motorized device 156 rotates the probe 110 in the rotational direction $M_1$ which will wind the helically-shaped shaft of the helical needle 112 into the tissue mass 128. The probe 110 is moved toward the tissue mass 128 such that the sharp tip 146 of the needle 112 penetrates the tissue wall 126 at entry point P. The motorized device 156 then rotates probe 110 in the rotational direction $M_1$, thereby winding the helically-shaped shaft 138 into the tissue mass 128. With the distal end 116 of probe 110 at the desired position within tissue mass 128, the motorized device 156 is stopped, and a thermal energy source (not shown) in probe 110 is energized. The temperature of the tissue mass 128 is monitored by means of the thermal sensors 152 on the helical needle 112. The thermal energy source of probe 110 is de-energized after the tissue mass 128 has been maintained at a sufficiently high temperature for a sufficiently long time that a substantial portion of the tissue mass 128 has coagulated. The directional switch 160 is set such that the motorized device 156 will rotate the probe 110 in the rotational direction $M_2$ which will wind the helically-shaped shaft 138 of the helical needle 112 out of the tissue mass 128. The motorized device 156 is started by means of the on/off switch 158 and the probe 110 is rotated in direction $M_2$, thereby winding the helically-shaped shaft 138 out of the tissue mass 128 and withdrawing probe 110 from the tissue mass 128.

Figure 5:
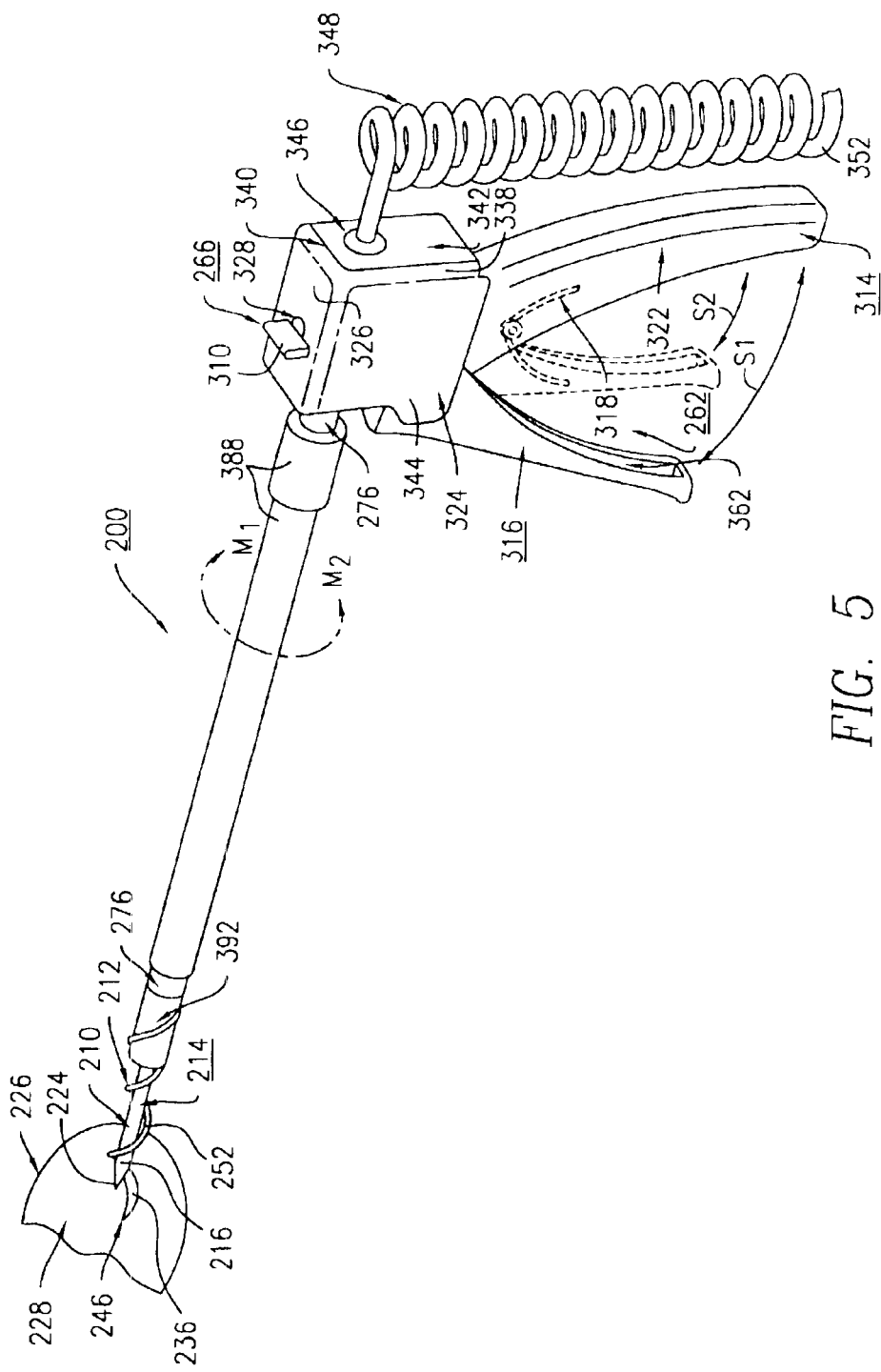
FIG. 5 is a perspective view of the surgical probe of FIG. 1 with a ratchet-type screw assembly constructed in accordance with a third exemplary embodiment of the present invention.
Figure 6:
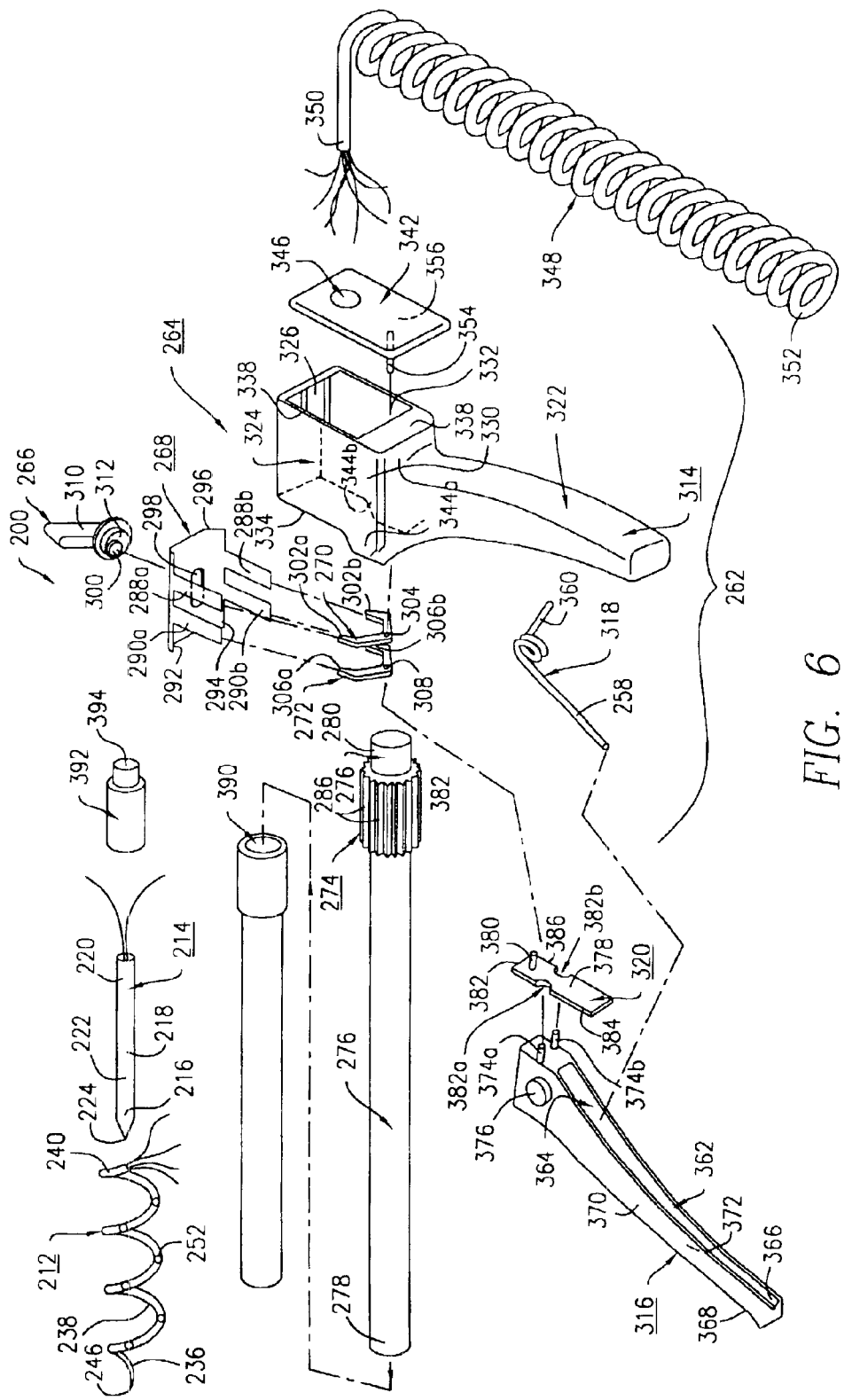
FIG. 6 is an exploded perspective view of the surgical probe and ratchet-type screw assembly of FIG. 5.

A third exemplary embodiment 200 of the present invention is shown in FIGS. 5 and 6. Elements shown in FIGS. 5 and 6 which correspond to the elements described above with reference to FIG. 1 have been designated by corresponding reference numbers increased by two hundred. Elements shown in FIGS. 5 and 6 that correspond to elements described above with respect to FIG. 4 have been designated by corresponding reference numbers increased by one hundred. The third exemplary embodiment 200 is constructed and operates in the same manner as the first exemplary embodiment 10, unless it is otherwise stated.

As can be seen in FIG. 5, the proximal end 220 of the probe 210 does not include a handle member 32 such as that included in the probe 10 of the first embodiment 10 (see FIG. 1). The proximal end 220 includes a ratchet-type screw assembly 262 for rotating the probe 210 in a rotational direction $M_1$ or an opposite rotational direction $M_2$, as required to insert or withdraw the probe 210 and helical needle 212 from the tissue mass 228.

Referring to FIGS. 5–10c, the ratchet-type screw assembly 262 includes a ratchet-gear sub-assembly 264 having a reversing lever 266, a ratchet spring 268, a pawl element 270, a ratchet element 272, a gear member 274 and a hollow shaft 276. The hollow shaft 276 includes a distal end 278, a proximal end 280 and an interior channel 282. The gear member 274 includes an axial opening 284 for receiving the proximal end 280 of shaft 276. The gear member 274 also includes a plurality of gear teeth 286 for engaging the pawl and ratchet elements 270, 272 The ratchet spring 268 includes an outer pair of spring arms 288a, 288b and an inner pair of spring arms 290a, 290b. Ratchet spring 268 also includes an upper wall 296 having opposing perimeter sides 292, 294 and an oval opening 298. The spring arms 288a, 290a are integrally attached to perimeter side 292 and the spring arms 288b, 290b are integrally attached to the perimeter side 294 (see FIGS. 6 and 7). Reversing lever 266 includes a tab element 300 that is adapted to be received within the oval opening 298 of the upper wall 296 of the ratchet spring 268.

Continuing to refer to FIGS. 5–10c, the pawl element 270 includes a pair of opposing gear engagement tabs 302a, 302b for interacting with the outer pair of spring arms 288a, 288b, respectively, and with the gear teeth 286 of the gear member 274 so as to prevent the gear member 274 from rotating against the selected rotational direction $M_1$, or $M_2$. The pawl element 270 also includes a centrally located pivot opening 304. The ratchet element 272 includes a pair of opposing gear engagement tabs 306a, 306b for interacting with the inner pair of spring arms 290a, 290b, respectively, and with the gear teeth 286 of the gear member 270 to drive the gear member in the selected rotational direction $M_1$, or $M_2$. The ratchet element 272 also includes a centrally located pivot opening 308. The reversing lever 266 includes a lever arm 310 and a cam element 312, wherein the tab element 300 is located in a position off-set from the center of the cam element 312 (see FIG. 6), and the lever arm 310 is located in a position off-set relative to the position of tab element 300. The cam element 312 of reversing lever 266 is used to shift the ratchet spring 268 in a side-to-side movement as reversing lever 266 is moved between a first position and a second position.

Referring now to FIGS. 6–9, the ratchet-type screw assembly 262 also includes a handle member 314, a pull lever 316, a return spring 318 and a guide bracket 320. The handle member 314 includes a handle section 322 and an integrally attached housing section 324 for holding and encasing the sub-assembly 264 therein. The housing section 324 includes an upper wall 326 having a mounting opening 328 therein, side walls 330, 332, a front wall 334 having a rectangular opening 336 therein, a rear wall 338 having a rectangular opening 340 therein, and a rear housing cover 342. The rectangular opening 340 receives the ratchet gear sub-assembly 264 therethrough and the rear housing cover 342 thereon. The mounting opening 328 of upper wall 326 receives the cam element 312 therethrough, such that the cam element 312 may alternately bias the spring arms 288a, 290a or the spring arms 288b, 290b of the ratchet spring 268 towards the gear member 274 as the reversing lever 266 is moved alternately between a first position and a second position. When the reversing lever 266 is in the first position, the cam element 312 also biases the spring arm 288a away from the side wall 330 of housing section 324, but does not bias spring arm 290a. When the reversing lever 266 is in the second position, the cam element 312 biases the spring arm 290b away from the side wall 332 of the housing section 324. The side wall 330 includes a hinge cover 344a and side wall 332 includes a hinge cover 344b, each hinge cover 344a, 344b being integrally connected to the corresponding side wall 330, 332 (see FIGS. 5 and 6). The housing cover 342 has a centrally located opening 346 for receiving an electrical cable 348 having a distal end 350 and a proximal end 352. The distal end 350 of the electrical cable 348 is inserted through the opening 346 of the housing cover 342 and the interior channel 282 of shaft 276. The distal end 350 of the electrical cable 348 is electrically connected to the proximal end 220 of probe 210 for providing electrical energy to the thermal energy source (not shown) within probe 210, and is electrically connected to the proximal end 240 of helical needle 212 for providing electrical energy to the thermal sensors 252 within helical needle 212. The housing cover 342 also includes an integrally attached pivot pin 354 positioned on an inner wall surface 356 of housing cover 342. The pivot pin 354 of housing cover 342 is received within the pivot opening 304 of pawl element 270, allowing the pawl element 270 to move independently from the ratchet element 272.

Figure 7:
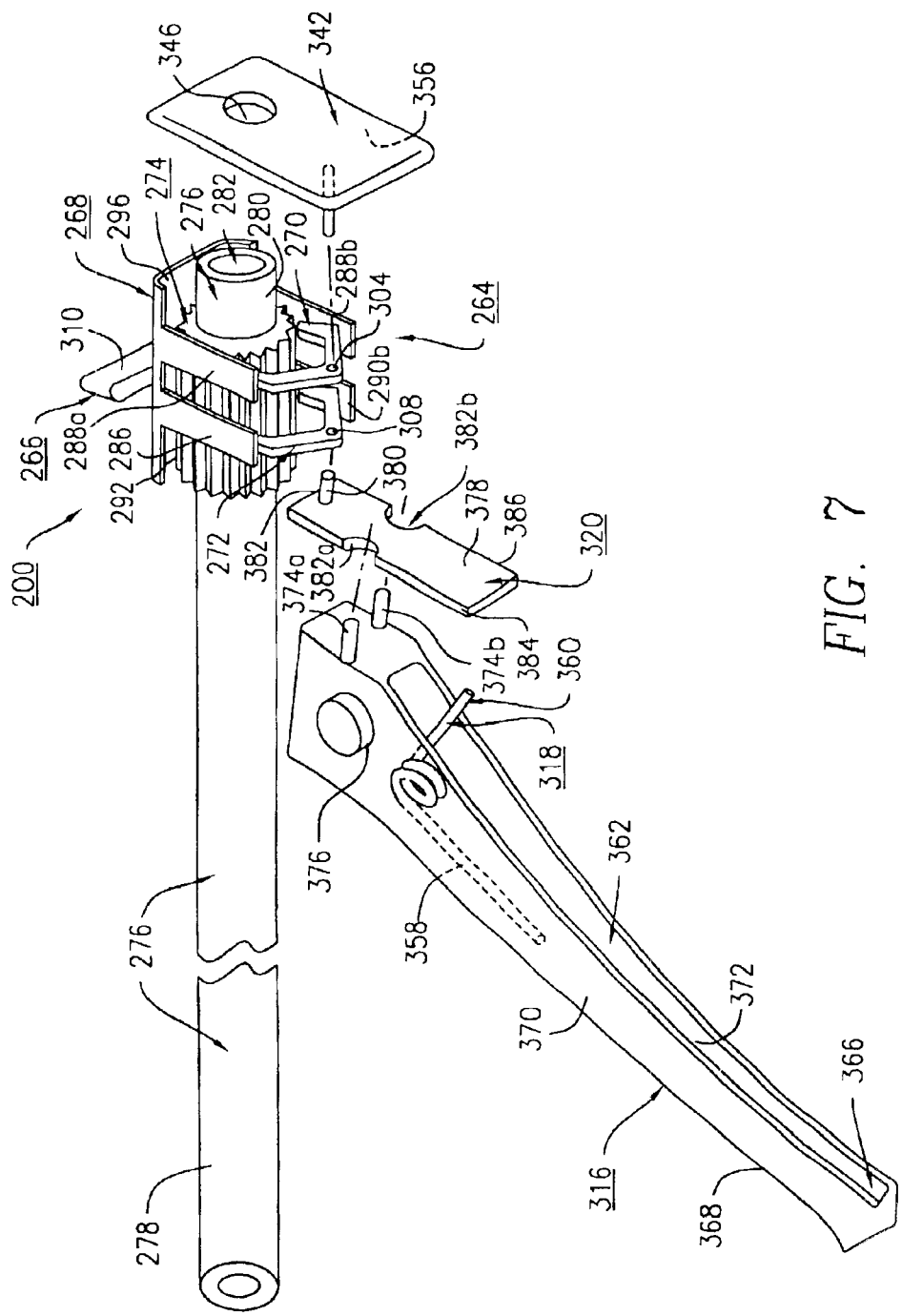
FIG. 7 is an exploded perspective view of the ratchet-type screw assembly of FIG. 5 showing elements of the assembly that attach a pull lever to a ratchet mechanism.

As shown in FIGS. 5–10a, the return spring 318 includes a first spring arm 358 and a second spring arm 360. The pull lever 316 includes a front grooved channel 362 having a distal end 364 and a proximal end 366, a front wall 368 and side walls 370, 372. Each of the side walls 370, 372 includes a tab pin 374a, 374b, respectively, thereon. Each of the side walls 370, 372 further includes a hinge pin 376a, 376b, respectively, thereon. Each of the hinge pins 376a, 376b are received within the corresponding hinge cover 344a, 344b, respectively, for connecting the pull lever 316 to the handle member 314 (see FIGS. 5, 6 and 10a). Referring to FIGS. 8 and 9, the first spring arm 358 of return spring 318 is positioned within the distal end 364 of the grooved channel 362 and the second spring arm 360 of return spring 318 is received within opening 336 on the front wall 334 of housing section 324 of handle member 314, in order to flex the pull lever 316 to an opened configuration $S_1$ relative to the handle section 322 of handle member 314. The guide bracket 320, as depicted in FIGS. 7 and 8, includes an inner wall surface 378 having an integrally attached pivot pin 380 thereon, being adjacent to an upper edge 382 of guide bracket 320. The guide bracket 320 also includes a pair of grooved notches 382a, 382b each being centrally positioned on side edges 384, 386, respectively. The pivot pin 380 of guide bracket 320 is received within the pivot opening 308 of ratchet element 272, allowing the ratchet element 272 to move independently from the pawl element 270. Each of the tab pins 374a, 374b of pull lever 316 are received within a corresponding grooved notch 382a, 382b on guide bracket 320, respectively, thus connecting the guide bracket 320 to the pull lever 316 and to handle member 314, as well as to the ratchet element 272 of the ratchet-gear sub-assembly 264 (see FIGS. 8, 9 and 10a). Referring again to FIGS. 7, 8 and 9, the return spring 318 interconnects the pull lever 316 with the guide bracket 320 and the housing section 324, of handle member 314, such that, when the pull lever 316 is squeezed toward the handle section 322 of handle member 314 (i.e, to position $S_2$), the pull lever 316 engages the ratchet-gear sub-assembly 264. The ratchet-gear sub-assembly 264 then advances and turns gear member 274 and shaft 276 in rotational direction $M_1$ or in rotational direction $M_2$, depending upon the position of reversing lever 266 and the resulting bias on spring 268 (see FIGS. 10a–10c).

Referring now to FIGS. 5 and 6, the ratchet-type screw assembly 262 further includes a sliding sleeve 388 having an interior channel 390 for slidably receiving shaft 276 therein, and a union connector 392 having an axial opening 394 for attaching and receiving the proximal end 220 of the probe 210 and the proximal end 240 of the helical needle 212 and connecting the respective proximal ends 220, 240 to the distal end 278 of shaft 276 (see FIG. 5).

In operation, the ratchet-type screw assembly 262 may be used to rotate the probe 210 and the helical needle 212 so as to insert or withdraw the probe 210 and the helical needle 212 from the tissue mass 228. The following example illustrates the application of the third embodiment 200 with particular attention to the operation of the ratchet-type screw assembly 264.

Figure 10A:
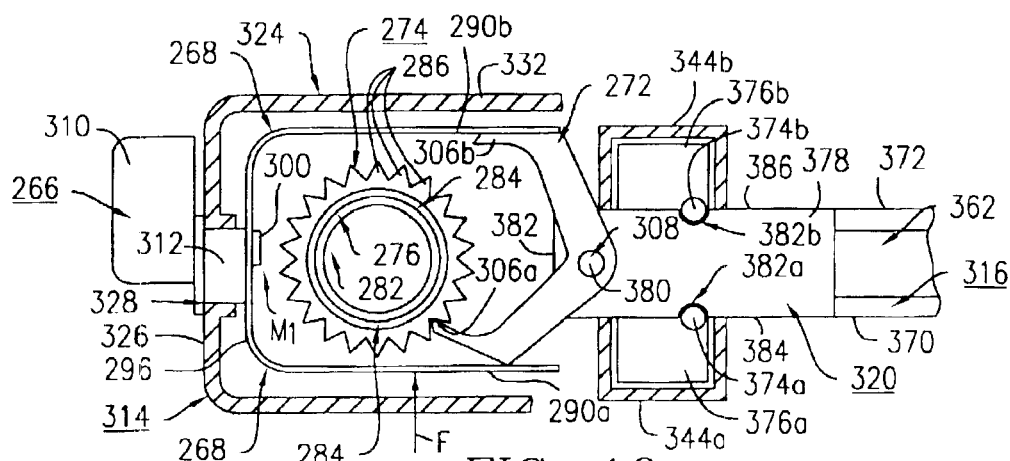
FIG. 10a is a sectional view of the ratchet-type screw assembly of FIG. 7 showing the configuration of the ratchet mechanism prior to actuation.
Figure 10B:
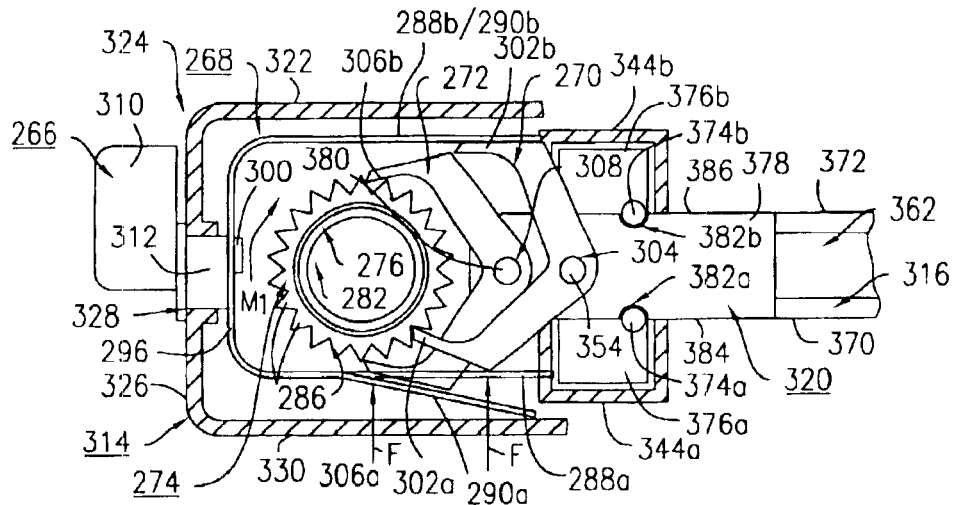
FIG. 10b is a sectional view of the ratchet-type screw assembly of FIG. 10a showing the configuration of the ratchet mechanism during actuation in a first rotational direction.
Figure 10C:
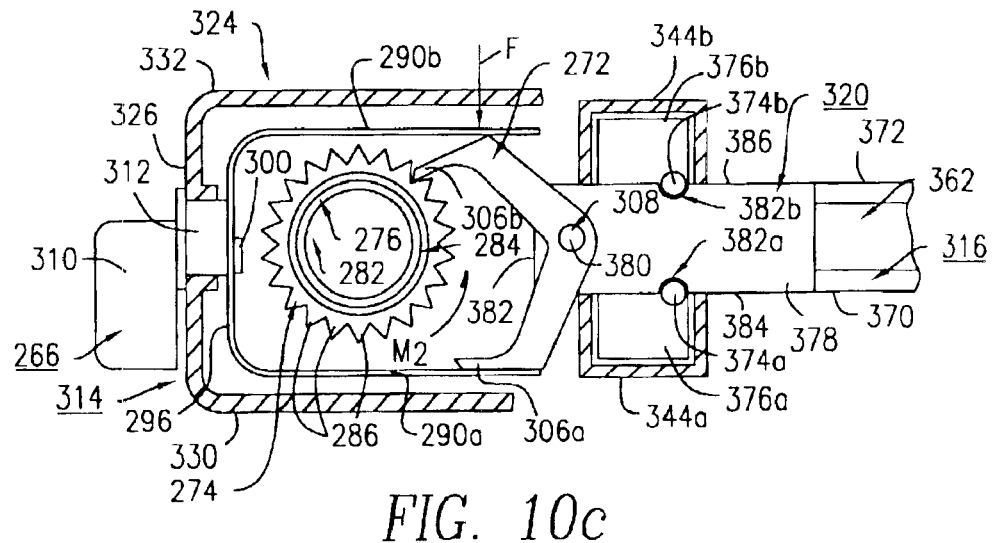
FIG. 10c is a sectional view of the ratchet-type screw assembly of FIG. 10b showing the ratchet mechanism configured for actuation in a second rotational direction opposite to the first rotational direction.

Referring now to FIGS. 10a, 10b, which show the ratchet-gear sub-assembly 264 as configured to rotate the probe 210 in the rotational direction $M_1$, it can be seen that the reversing lever 266 is set in a first position so that cam element 312 of reversing lever 266 biases the spring arms 288a, 290a towards the gear member 274. The spring arm 288a contacts the gear engagement tab 302a of pawl element 270, thereby moving the gear engagement tab 302a such that it engages one of the gear teeth 286 of gear member 274. By engaging gear tooth 286, gear engagement 302a prevents the backward rotation of gear member 274 (i.e., rotation in direction $M_2$). At the same time, the spring arm 290a contacts the gear engagement tab 306a of ratchet element 272, thereby moving the gear engagement tab 306a to engage one of the gear teeth 286 of gear member 274. The gear engagement tab 306a engages its corresponding gear tooth 286 such that pushing ratchet element 272 toward gear member 274 will cause gear member 274 to rotate in rotational direction $M_1$. The spring force F from the spring arms 288a, 290a keeps the pawl and ratchet elements 270, 272, respectively, in contact with the gear member 274 at all times. The direction of rotation may be changed to rotational direction $M_2$ by setting reversing lever 266 to a second position (see FIG. 10c) which causes the cam element 312 to bias the spring arms 288b, 290b of the ratchet spring 268 towards the gear member 274. The spring arm 288b contacts the gear engagement tab 302b of pawl element 270, thereby moving the gear engagement tab 302b such that it engages one of the gear teeth 286 of gear member 274 to prevent the backward rotation of gear member 274 (i.e., rotation in direction $M_1$). The spring arm 290b contacts the gear engagement tab 306b of ratchet element 272, thereby moving the gear engagement tab 306b to engage one of the gear teeth 286 of gear member 274. Because the gear engagement tab 306b is on the opposite side of the gear member 274 from engagement tab 306a, pushing ratchet element 272 toward gear member 274 will cause gear member 274 to rotate in the opposite rotational direction $M_2$.

For the purpose of this illustrative example, it is understood that assembly 262 was set to rotate probe 210 in rotational direction $M_1$ by setting reversing lever 266 to a first position prior to pointing the distal end 216 of the probe 210 with the sharp tip 246 of helical needle 212 in contact with the tissue wall 226. The operator then proceeds to squeeze the pull lever 316 towards the handle section 322 from a first position $S_1$ to a second position $S_2$ several times, thereby pushing ratchet element 272 toward gear member 274 by means of the interconnected elements handle 316 and guide plate 320. The rotation of the probe 210 causes the helically-shaped shaft 238 of helical needle 212 to wind into the tissue mass 228, thereby advancing the probe 210 and the helical needle 212 into the tissue mass 228. After completion of the thermal treatment, the operator then sets the reversing lever in a second position, reversing the direction of rotation, and squeezes the pull lever 316 towards the handle section 322, as described above. The probe 210 is rotated in rotational direction M2, thereby winding helically-shaped shaft 238 out of the tissue mass 228 such as to remove the probe 210 and the helical needle 212 from the tissue mass 228.

The use of a helical needle 12 in combination with a probe 10, as described above, presents numerous advantages compared to the use of the probe 10 by itself. For example, the relatively thin distal end 36 of helical needle 12 penetrates more readily into the rubbery or calcified tissue of a myoma, tumor or other unwanted growth (i.e, tissue mass 28) than does the thicker distal end 16 of probe 10. The helical shape of the shaft 38 of the helical needle 12 causes the helical needle 12 to advance into the tissue mass 28 in an axial direction as it is rotated, pulling the probe 10 in the same direction. The probe 10 can, therefore, be more readily advanced into the tissue mass 28 by rotation when the angle of entry or the condition of the tissue would make it difficult to insert the probe 10 by pushing it in an axial direction. Under typical circumstances, rotational force alone will be sufficient to drive the probe into or out of the tissue mass. The assistance provided to the entry of probe 10 also enables the use of probes having larger diameters than the one (1) mm probes that are presently preferred. Another advantage may be realized because the helical shape of the shaft 38 of the helical needle 12 causes the helical needle 12 to resist being moved within the tissue mass 28 by forces applied in the axial or lateral directions. This resistance to movement acts to stabilize the position of probe 10 within the tissue mass 28 during treatment, reducing the likelihood that the probe 10 will be accidentally withdrawn from the intended treatment location. Moreover, the geometry of the helically-shaped shaft 38 causes the probe 10 to be advanced by a predetermined distance with each complete rotation of the affixed helically-shaped shaft 38. This geometrical relationship allows the depth to which the probe 10 penetrates the tissue mass 28 to be controlled by precisely rotating the probe 10 and helical needle 12. Such precise rotation may be provided by the ratchet-type screw device 262 or other mechanical devices adapted to rotate the probe 10 by predetermined amounts. The helical needle 12 may also serve as a carrier for thermal sensors for monitoring the temperature of the tissue mass 28 during thermal treatment, and, thereby, providing a means to control the temperature of the tissue mass 28 and the progress of the treatment.

The combination of probe and helical needle disclosed herein is not limited to uses in laparoscopic surgery. It may also be used advantageously in open surgery, hysteroscopic surgery or for entry through natural body orifices such as the mouth, the ear, the vagina, the uterus, the rectum, or the penis.

It will be understood that the embodiments described herein are merely exemplary and that a person skilled in the art may make many variations and modifications without departing from the spirit and scope of the invention. For example, the helical needle 12 may be solid instead of having an interior channel 44. The helical needle 112 may also be solid and the thermal sensors 152 and their respective conductive leads 154a and 154b attached to the exterior wall surface 142 of the helical shaft section 138 of helical needle 112. Alternatively, in embodiments where the helical needle 112 has an interior channel 144, the openings 150 may be omitted and the thermal sensors 152 and conductive leads 154a, 154b embedded in a plastic rod or tube within the interior channel 144. The helical needle 112 may also be used as a carrier for sensors other than the thermal sensors 152. The probe 10 may be provided with means for rotatably inserting and removing the probe 10 other than the motor device 156 or ratchet-type screw assembly 262. All such variations and modifications, including those discussed above, are intended to be included within the scope of the invention as defined in the appended claims.

We claim:

1. A surgical device, comprising a surgical probe having a substantially straight shaft section and a distal end;

a helical needle having a distal end, the helical needle being affixed to the probe such that the distal end of the helical needle extends beyond the distal end of the probe;

end and a proximal end opposite the distal end of the probe; and driving means, located at the proximal end of the surgical device, for selectively rotating the surgical device in a first rotational direction and in a second rotational direction opposite to the first rotational direction, the driving means including a ratchet assembly having a ratchet gear, a ratchet having a first gear engagement tab for rotating the ratchet gear in the first rotational direction and a second gear engagement tab for rotating the ratchet gear in the second rotational direction, a pawl having a first gear engagement tab for preventing the rotation of the ratchet gear in the second rotational direction and a second gear engagement tab for preventing the rotation of the ratchet gear in the first rotational direction, the pawl being movable independently of the ratchet, a ratchet spring member having a first side piece and a second side piece, the first side piece and the second side piece being substantially parallel, the ratchet gear being positioned at a location intermediate between the first side piece and the second side piece, a reversing lever connected to the ratchet spring member such as to bias the first side panel toward the ratchet gear when the reversing lever is in a first position and bias the second side panel toward the ratchet gear when the reversing lever is in a second position, such that the first side panel acts on the pawl and ratchet gear when the reversing lever is in the first position, thereby engaging the first gear engagement tab of the ratchet with the ratchet gear, and the second side panel acts on the pawl and ratchet gear when the reversing lever is in the second position thereby engaging the second gear engagement tab of the pawl with the ratchet gear and the second gear engagement tab of the ratchet with the ratchet gear, and a movable handle adapted such that the ratchet gear is rotated by movement of said handle.

* * * * *